United States Patent
Kawano et al.

(10) Patent No.: US 9,592,015 B2
(45) Date of Patent: Mar. 14, 2017

(54) RADIOGRAPHIC APPARATUS

(71) Applicant: SHIMADZU CORPORATION, Kyoto-shi, Kyoto (JP)

(72) Inventors: Masahiro Kawano, Kyoto (JP); Tomoharu Okuno, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 69 days.

(21) Appl. No.: 14/366,639

(22) PCT Filed: Dec. 5, 2012

(86) PCT No.: PCT/JP2012/007797
§ 371 (c)(1),
(2) Date: Jun. 18, 2014

(87) PCT Pub. No.: WO2013/099115
PCT Pub. Date: Jul. 4, 2013

(65) Prior Publication Data
US 2014/0341348 A1 Nov. 20, 2014

(30) Foreign Application Priority Data
Dec. 27, 2011 (JP) .................... 2011-286034

(51) Int. Cl.
*A61B 6/08* (2006.01)
*A61B 6/06* (2006.01)
(Continued)

(52) U.S. Cl.
CPC .............. *A61B 6/08* (2013.01); *A61B 6/06* (2013.01); *A61B 6/10* (2013.01); *A61B 6/542* (2013.01); *A61B 6/4283* (2013.01)

(58) Field of Classification Search
CPC .... A61B 6/06; A61B 6/08; A61B 6/10; A61B 6/542
See application file for complete search history.

(56) References Cited

U.S. PATENT DOCUMENTS

2008/0317212 A1* 12/2008 Kuehn ............... A61B 6/06 378/151
2010/0098215 A1* 4/2010 Takahashi ............ A61B 6/06 378/147

FOREIGN PATENT DOCUMENTS

JP 2010-094212 A 4/2010
JP 2011104154 A * 6/2011

OTHER PUBLICATIONS

International Search Report PCT/JP2012/007797 dated Mar. 12, 2013.

* cited by examiner

*Primary Examiner* — Glen Kao
(74) *Attorney, Agent, or Firm* — McDermott Will & Emery LLP

(57) ABSTRACT

The disclosure provides a radiographic apparatus that allows suppression of needles radiation exposure to a subject. Specifically, the disclosure includes an X-ray tube, a collimator, and a visible light source. The spread of visible light beams through the collimator opening too largely may not possibly conform to the spread of radiation. Such a situation may occur when the apparatus is provided with the X-ray tube that emits narrow radiation. In order to avoid such a situation, the disclosure sets an upper limit of a degree of opening as an upper limit of a degree of opening of the collimator. With a construction of the disclosure, there is no need to perform further radiography. This achieves the radiographic apparatus that allows suppression of needless radiation exposure to a subject.

8 Claims, 4 Drawing Sheets

(51) Int. Cl.
*A61B 6/10* (2006.01)
*A61B 6/00* (2006.01)

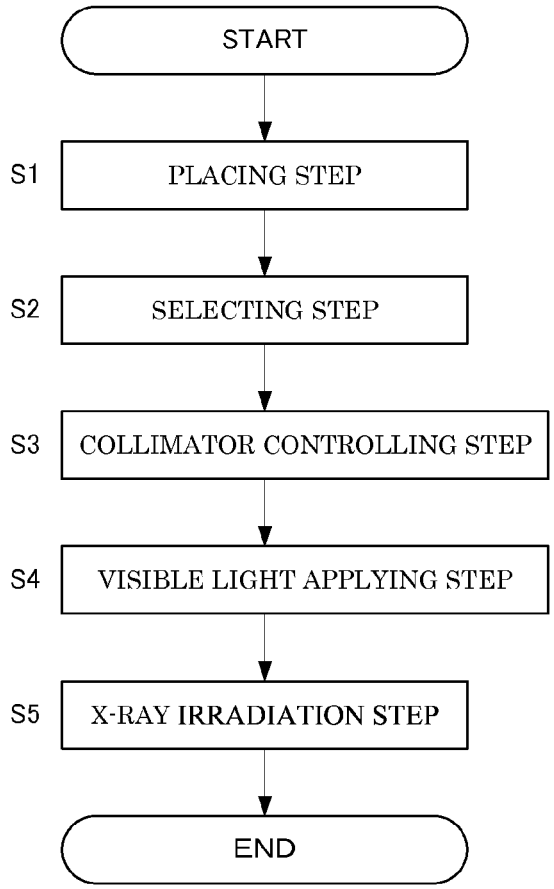
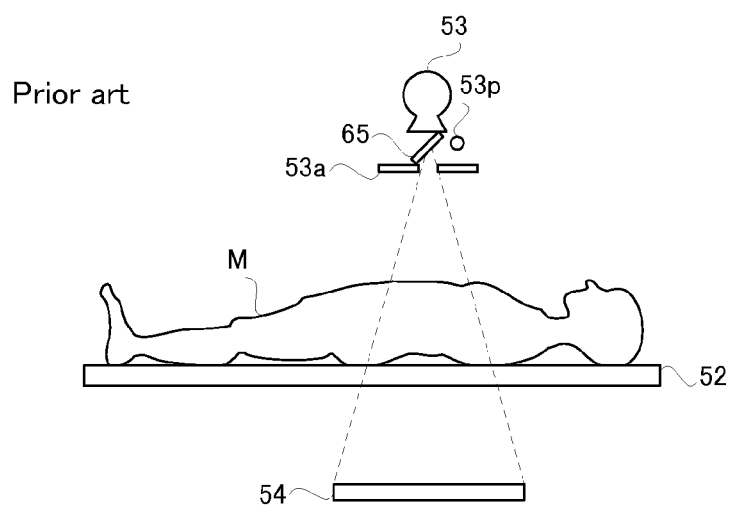

RADIOGRAPHIC APPARATUS

RELATED APPLICATIONS

This application is the U.S. National Phase under 35 U.S.C. §371, of International Application No. PCT/JP2012/007797, filed on Dec. 5, 2012, which in turn claims the benefit of Japanese Application No. 2011-286034, filed on Dec. 27, 2011, the disclosures of which Applications are incorporated by reference herein.

TECHNICAL FIELD

The present invention relates to a radiographic apparatus for performing fluoroscopy to a subject. More particularly, the present invention is directed to a radiographic apparatus having a collimator for restricting an irradiation direction of radiation.

BACKGROUND ART

Medical institutions are equipped with a radiographic apparatus configured to emit radiation to image a subject M. Such a radiographic apparatus includes a radiation source 53 and a cassette 54 as illustrated in FIG. 9. The radiation source 53 emits radiation, and the cassette 54 detects the radiation. A top board 52 is provided between the radiation source 53 and the cassette 54. The top board 52 supports the subject M placed thereon.

The radiation source 53 has a collimator 53a attached thereto. The collimator 53a restricts an irradiation area of radiation. The radiation from the radiation source 53 passes through the collimator 53a, whereby the spread of the radiation is restricted. Then the restricted radiation is applied to the subject M.

The radiation source 53 also includes an optical lamp 53p for confirming the irradiation area of the radiation. The optical lamp 53p is disposed behind the collimator 53a, seen from the top board 52, together with a mirror 65. Similarly to the radiation, light beams from the optical lamp 53p pass through the collimator 53a to the top board 52.

When an operator issues a command to turn on the optical lamp 53p prior to irradiation with radiation, the optical lamp 53p is turned on such that visible light beams whose spread is restricted by the collimator 53a are applied to a part of the subject M. Here, the part of the subject M irradiated by the optical lamp 53p corresponds to an area to be irradiated with radiation.

The radiation from the radiation source 53 is not visible light beams. Consequently, an area of the subject M irradiated with the collimated radiation is invisible. Accordingly, the operator turns on the optical lamp 53p prior to the irradiation with radiation, thereby confirming the area of the subject M irradiated with the radiation. Then the operator controls a degree of opening of the collimator 53a while the optical lamp 53p is turned on, achieving control of the irradiation area of the radiation. Japanese Patent Publication No. 2010-094212A describes a construction with such a collimator 53a.

PATENT LITERATURE

Patent Literature 1

Japanese Patent Publication No. 2010-094212A

SUMMARY

Technical Problem

The conventional radiographic apparatus has a drawback as under. Specifically, the conventional radiographic apparatus sets the collimator 53a regardless of specifications of the radiation source 53. This leads to needless exposure to the subject.

The radiation source 53 is manufactured so as to restrict an irradiation direction of radiation without the collimator 53a. That is, the radiation source 53 has a maximum irradiation width. This causes a ceiling that no radiation is applicable any more however the collimator 53a may operate. The maximum irradiation width of radiation in the radiation source 53 varies depending on types of the radiation source 53.

It is not determined into which radiation source 53 the collimator 53a is incorporated upon manufacture. As a result, the collimator 53a is manufactured with a sufficient degree of opening so as to operate satisfactorily when incorporated into any radiation source 53.

Here, it is assumed that the radiographic apparatus is manufactured with the above collimator 53a being attached to a radiation source 53 having the small spread of radiation. In such an apparatus, when radiation is emitted with the collimator 53a fully opened, the radiation emitted from the radiation source 53 passes through the collimator 53a without reaching the collimator 53a. That is because the radiation emitted from the radiation source 53 is narrower than an expanding width of the collimator 53a in a full-open state.

Next, radiography with such an apparatus is to be considered. An operator confirms the spread of the radiation using an optical lamp 53p attached to the collimator 53a prior to radiography. The light from the optical lamp 53p sufficiently spreads for faithfully representing the degree of opening of the collimator 53a.

Consequently, when the optical lamp 53p is turned on, the collimator 53a in the full-open state restricts and emits visible light beams from the optical lamp 53p. In fact, however, radiation is emitted not to an irradiation area of the visible light beams but to an area narrower than the irradiation area of the visible light beams. As above, an irradiation width of the visible light from the optical lamp 53p does not conform to that of radiation. Such a phenomenon may occur. In other words, radiation is narrower than the visible light.

However, the operator continuously performs radiography without noticing such discrepancy. That is, the operator performs radiography while believing the radiation entering into the area of the subject irradiated with the visible light beams. Accordingly, an image is not obtainable having a site of interest of the subject appearing desirably. This requires further radiography. In other words, the conventional apparatus causes needless exposure to the subject.

The present invention has been made regarding the state of the art noted above, and its primary object is to provide a radiographic apparatus that allows suppression of needles radiation exposure to a subject.

Solution to Problem

The present invention adopts the following construction for overcoming the above drawback. One embodiment of the present invention discloses a radiographic apparatus. The radiographic apparatus includes a radiation source configured to emit radiation, a detecting device configure to detect radiation passing through a subject, a collimator configured to restrict the spread of the radiation emitted from the radiation source, a collimator activating device configured to activate the collimator to change a degree of opening of the collimator, a visible light source provided on the collimator and configured to emit visible light beams, a visible light source controller configured to control the visible light source, and a collimator controller. The collimator controller is configured to control the collimator activating device so as the spread of the radiation not to exceed an upper limit of the degree of opening, the degree corresponding to a minimum degree of opening, at which the spread of the radiation does not increase any more when the degree of opening of the collimator gradually increases while the radiation is emitted.

Operation and Effect

The embodiment of the present invention includes the radiation source, the collimator, and the visible light source. The collimator is provided for restricting the spread of radiation. The visible light source is provided for representing the area to which radiation is applied instead of the radiation source by applying visible light passing through the collimator, the radiation from the radiation source being invisible. With some type of the radiation source, when the collimator opens too largely, the spread of the visible light beams through the collimator may not possibly conform to the spread of radiation. Such a situation may occur when the apparatus is provided with the radiation source that emits narrow radiation.

In order to avoid such a situation, the embodiment of the present invention sets the upper limit of the degree of opening as an upper limit of the degree of opening of the collimator. The degree of opening of the collimator gradually increases while radiation is emitted to reach the minimum degree of opening at which the spread of X-ray beams does not increase any more. The minimum degree corresponds to the upper limit of the degree of opening. In the embodiment of the present invention, the irradiation area of the visible light beams always conforms to the irradiation area by the radiation source. Accordingly, there is no need to perform further radiography. This achieves the radiographic apparatus that allows suppression in needless exposure of radiation to the subject.

Moreover, the embodiment of the radiographic apparatus further includes an input device via which an operator inputs a command, an alarm-activating device configured to activate an alarm to the operator; and an alarm-activation controller configured to issue a command to the alarm-activating device to activate the alarm. The alarm-activation controller controls the alarm-activating device to activate the alarm when the degree of opening of the collimator is controlled to exceed the upper limit of the degree of opening via the input device. Such is more desirable.

Operation and Effect

The above construction describes one example of the radiographic apparatus in the embodiment of the present invention. That is, the alarm is activated when the degree of opening of the collimator is controlled so as to exceed the upper limit of the degree of opening. This obtains the apparatus with a higher degree of safety, ensuring to suppress needless exposure.

Moreover, in the embodiment of the radiographic apparatus, the collimator controller informs the alarm-activation controller so as to activate the alarm when a required degree of opening exceeds the upper limit of the degree of opening, the required degree of opening being a degree of opening of the collimator required upon radiography to be conducted by the operator. Such is more desirable.

Operation and Effect

The above construction describes one example of the radiographic apparatus in the embodiment of the present invention. That is, the alarm is activated when the degree of opening of the collimator required upon radiography to be conducted by the operator exceeds the upper limit of the degree of opening. This obtains accurate informing to the operator.

Moreover, the radiographic apparatus of the embodiment further includes a storing device configured to store a plurality of upper limits of the degrees of opening in association with types of the radiation source, and a radiation source controller configured to control the radiation source. The radiation source controller outputs type information representing one of the types of the radiation source to the collimator controller. The collimator controller reads out one of the plurality of upper limits of the degrees of opening, corresponding to the obtained type information, from the storing device. Such is more desirable.

Operation and Effect

The above construction describes one example of the radiographic apparatus in the embodiment of the present invention. That is, the collimator controller reads out the upper limit of the degree of opening corresponding to the type of the radiation source. This achieves the apparatus with more flexibility. Specifically, any type of the radiation source provided in the apparatus ensures to control the collimator in accordance with the upper limit of the degree corresponding to the type of the radiation source.

Advantageous Effects of Invention

The embodiment of the present invention includes the radiation source, the collimator, and the visible light source. When the collimator opens too largely, the spread of the visible light beams through the collimator may not possibly conform to the spread of radiation. Such a situation may occur when the apparatus is provided with the radiation source that emits narrow radiation. In order to avoid such a situation, the embodiment of the present invention sets the upper limit of the degree of opening representing the upper limit of the degree of opening of the collimator. With the embodiment of the present invention, there is no need to perform further radiography. This achieves the radiographic apparatus that allows suppression in needless exposure of radiation to the subject.

BRIEF DESCRIPTION OF DRAWINGS

FIG. 8 is a flow chart illustrating operation of the X-ray apparatus according to the embodiment.

FIG. 9 illustrates a conventional X-ray apparatus.

DESCRIPTION OF EMBODIMENTS

The following describes a concrete example as an embodiment for carrying out the present invention.

Embodiment 1

One embodiment of the present invention is to be described as under. X-rays in the embodiment correspond to radiation in the present invention.

<Whole Construction of X-Ray Apparatus>

Figure 1:
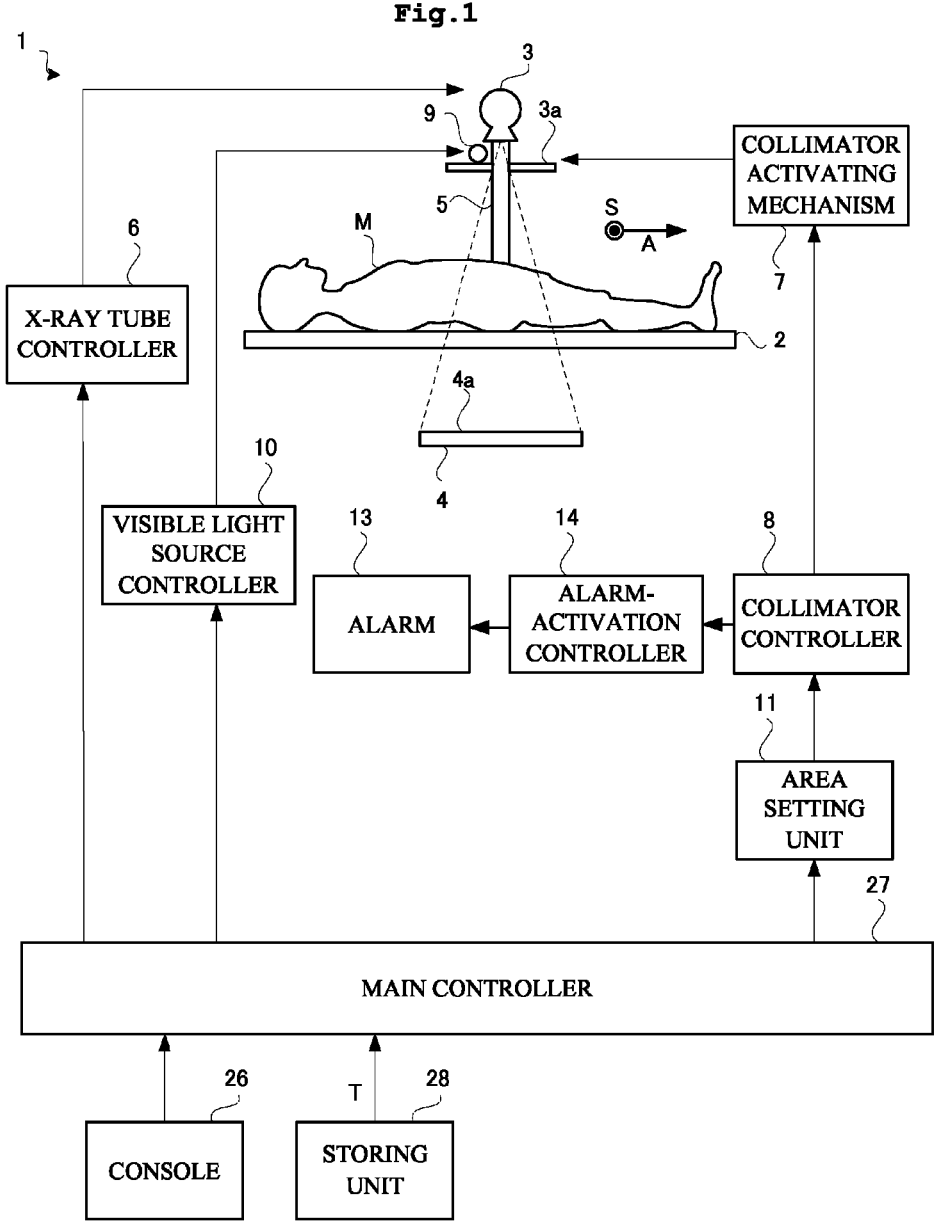
FIG. 1 is a function block diagram illustrating an X-ray apparatus according to one embodiment.

Firstly, an X-ray apparatus 1 according to Embodiment 1 is to be described. As illustrated in FIG. 1, an X-ray apparatus 1 includes a top board 2 configured to support a subject M placed thereon in a supine position, an X-ray tube 3 disposed above the top board 2 (at a first face side) and configured to emit X-rays, and a cassette 4 disposed below the top board 2 (at a second face side) and configured to detect X-rays. The cassette 4 is rectangular having four sides along either a body axis direction A or a body side direction S of the subject M. The X-ray tube 3 emits X-rays in a quadrangular pyramid shape to the cassette 4. An entire surface of the cassette 4 receives X-rays. A strut 5 extends from below the top board 2 (from the second face side) to above the top board 2 (to the first face side). The strut 5 supports the X-ray tube 3. The X-ray tube 3 corresponds to the radiation source in the present invention. The cassette 4 corresponds to the radiation detecting device in the present invention.

Figure 2:
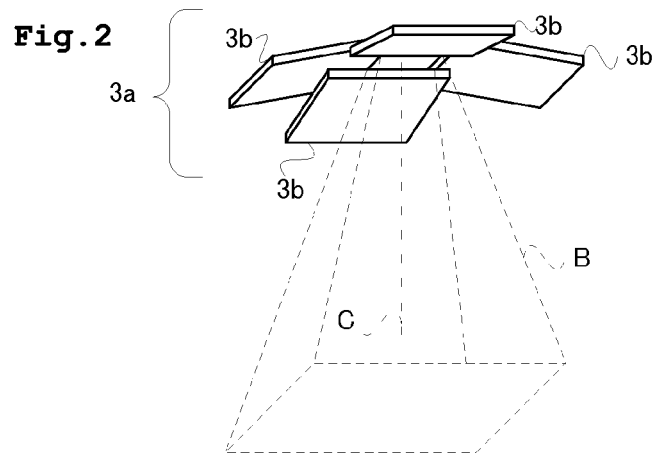
FIG. 2 is a perspective view illustrating a collimator according to the embodiment.

The X-ray tube 3 is provided with a collimator 3a (see FIG. 1). The collimator 3a restricts an irradiation area of X-rays. The collimator 3a has an adjustable degree of opening. As illustrated in FIG. 2, the collimator 3a has one pair of shielding vanes 3b that moves in a mirror-image symmetrical manner relative to the center axis C, and has another pair of shielding vanes 3b that similarly moves in a mirror-image symmetrical manner relative to the center axis C. Movement of the shielding vanes 3b of the collimator 3a allows not only irradiation of an entire detecting surface 4a of the cassette 4 with X-rays B in a cone shape, but also irradiation of only a center portion of the detecting surface 4a with X-rays B in a fan shape. Here, the center axis C represents the center of X-rays B. One pair of the shielding vanes 3b controls the spread of the quadrangular pyramid X-rays B in the body axis direction A. The other pair of the shielding vanes 3b controls the spread of the X-rays B in the body side direction S. When the X-ray tube 3 moves, the collimator 3a moves along with the movement of the X-ray tube 3 accordingly. A collimator activating mechanism 7 (see FIG. 1) changes a degree of opening of the collimator 3a through activating the shielding vanes 3b. A collimator controller 8 is provided for controlling the collimator activating mechanism 7. The collimator activating mechanism 7 corresponds to the collimator activating device in the present invention. The collimator controller 8 corresponds to the collimator activation controller in the present invention. Here, FIG. 2 illustrates the shielding vanes 3b, and a visible light source 9 and a mirror 15 of the collimator 3a are omitted. These elements are to be mentioned later.

An X-ray tube controller 6 (see FIG. 1) is provided for controlling the X-ray tube 3 with a given tube current, a given tube voltage, and a given pulse width. The X-ray tube controller 6 controls the X-ray tube 3 to emit X-rays. Then, the X-rays pass through the subject M to enter into the detecting surface 4a of the cassette 4. The cassette 4 contains an X-ray sensitive film. Accordingly, when the X-rays are applied to the film, a fluoroscopic image of the subject M is printed on the film. Here, the X-ray tube controller 6 corresponds to the radiation source controller in the present invention.

An area setting unit 11 sets a detection area of the cassette 4 where X-rays are detected. The area setting unit 11 is to be described. When the operator inputs a type of the cassette 4 to be used for radiography to a console 26, information representing the type of the cassette 4 is sent to the area setting unit 11. The area setting unit 11 refers to a table stored in a storing unit 28, the table being associated with the cassette 4 and a length of the film corresponding to the cassette 4, thereby obtaining the length of a film of the cassette 4 to be used for radiography. The length of the film is a length of the subject M in the body axis direction, and thus corresponds to an area where the cassette 4 detects X-rays. The area setting unit 11 sets this area as a detection area where X-rays are detected. The console 26 is used for inputting commands from the operator. The area setting unit 11 corresponds to the area setting device in the present invention. The console 26 corresponds to the input device in the present invention. The storing unit 28 corresponds to the storing device in the present invention.

<Regarding Visible Light Source>

As illustrated in FIG. 1, the visible light source 9 is provided on the collimator 3a. The visible light source 9 emits visible light beams. The visible light beams pass through a space between the shielding vanes 3b of the collimator 3a, whereby a part of the subject M is irradiated with the visible light beams. Similarly, X-rays from the X-ray tube 3 pass through the space between the shielding vanes 3b of the collimator 3a, whereby a part of the subject M is irradiated with the X-rays. Accordingly, the part of the subject M irradiated by the visible light source 9 conforms to the part of the subject M irradiated with X-ray beams from the X-ray tube 3. The visible light from the visible light source 9 is visible by the operator. Consequently, the operator can confirm visually an area (irradiation area or an irradiation field) of the subject M to which X-rays are applied prior to X-ray radiography. A visible light source controller 10 is provided for controlling the visible light source 9. The visible light source controller 10 corresponds to the visible light source controller in the present invention.

Figure 3:
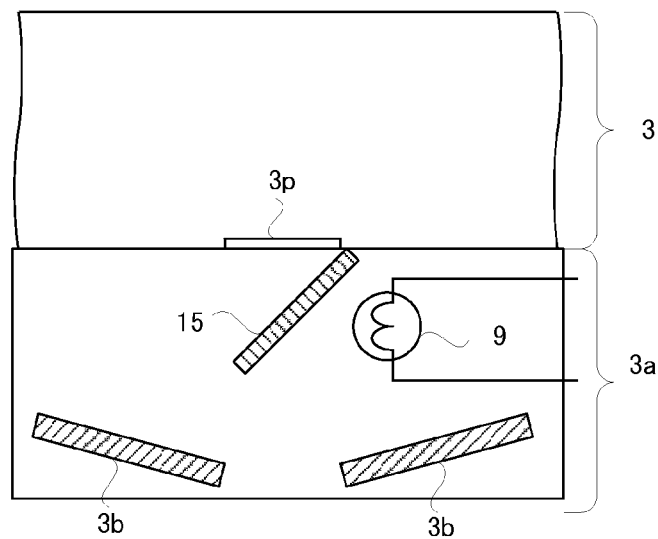
FIG. 3 is a sectional view illustrating a visible light source according to the embodiment.

The following describes a positional relationship between the X-ray tube 3 and the collimator 3a. FIG. 3 is a schematic view illustrating a positional relationship of the elements. The X-ray tube 3 is provided with an emitting hole 3p through which X-rays are emitted. The collimator 3a is provided with a mirror 15 inclined relative to the emitting hole 3p. The collimator 3a includes the visible light source 9. The visible light source 9 is disposed at the position as a mirror image of the X-ray tube 3 in a focus position by the mirror 15, seen from a subject M.

When the visible light source 9 is turned on, the visible light beams are emitted. The visible light beams are reflected on the mirror 15 to travel toward the collimator 3a. Thereafter, the collimator 3a restricts the spread of the visible light beams, whereby the visible light beams with a cone shape are generated. The cone visible light beams are outputted to the subject M.

When the visible light source 9 is turned off, X-rays are emitted from the X-ray tube 3. The X-rays pass through the mirror 15 toward the collimator 3a. Thereafter, the collimator 3a restricts the spread of the X-rays, whereby the X-ray beams with a cone shape are generated. The cone X-ray beams are outputted to the subject M. The visible light beams and the X-ray beams travel toward the subject M while spreading in the same manner unless the shielding vanes 3b of the collimator 3a move.

<Unconformity of Visible Light Beam and X-Ray Beam>

According to the above description, the part of the subject M irradiated by the visible light source 9 conforms to that irradiated with the X-ray beams from the X-ray tube 3. However, this is not always so. Specifically, the visible light beams may possibly be emitted more widely than the X-ray beams depending on types of X-ray tube 3. The following describes a reason why such a drawback occurs.

Figure 4:
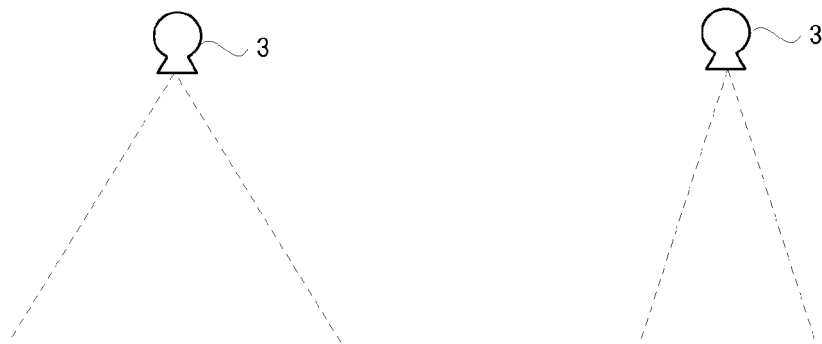
FIG. 4 is a schematic view illustrating the spread of X-rays emitted from an X-ray tube according to the embodiment.

FIG. 4 illustrates different types of X-ray tube 3. The X-ray tube 3 on the left of FIG. 4 has a large emitting hole 3p, allowing emission of wide X-ray beams. On the other hand, the X-ray tube 3 on the right of FIG. 4 has a small emitting hole 3p, merely allowing emission of narrow X-ray beams. As noted above, the X-ray tube 3 emits X-ray beams with various widths in accordance with variations in design, such as a dose of emittable X-rays and a weight.

Figure 5:
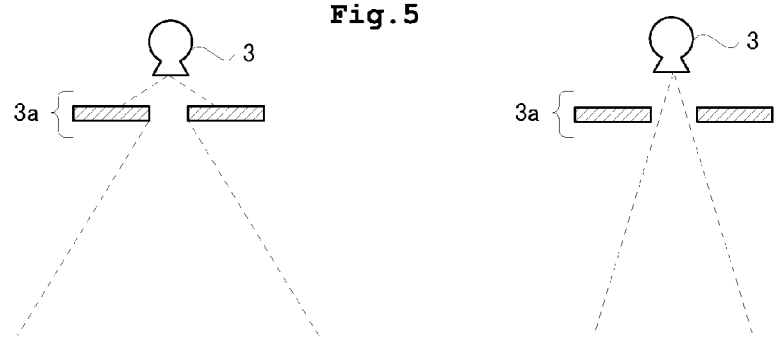
FIGS. 5 to 7 are schematic views each illustrating operation of a collimator controller according to the embodiment.

FIG. 5 illustrates X-ray beams from two types of X-ray tubes 3 passing through the collimator 3a. Here, the collimator 3a in FIG. 5 is fully opened. The X-ray tube 3 on the left of FIG. 5 allows emission of wide X-ray beams. The X-ray beams are too wide for entirely passing through the collimator 3a. Consequently, the X-ray beams emitted from the X-ray tube 3 pass through the fully-opened collimator 3a while the spread thereof is restricted. On the other hand, the X-ray tube 3 on the right of FIG. 5 merely allows emission of narrow X-ray beams. The X-ray beams are sufficiently narrow for entirely passing through the collimator 3a. Consequently, the X-rays emitted from the X-ray tube 3 pass through the fully-opened collimator 3a with no restriction to the spread. As noted above, the X-ray beams from some type of the X-ray tube 3 may pass through the fully-opened collimator 3a without reaching the collimator 3a.

Figure 6:
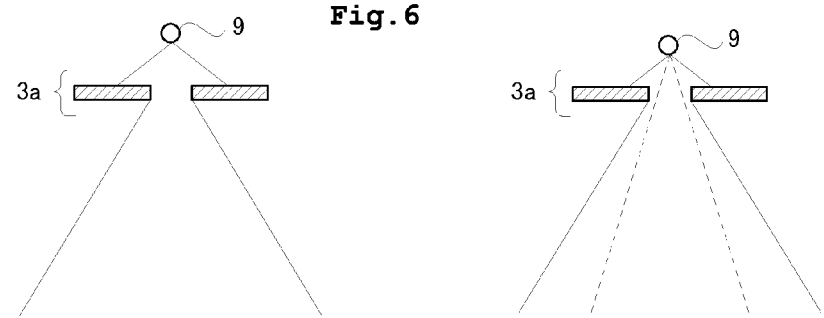

FIG. 6 illustrates the visible light beams emitted from the visible light source 9. In this drawing, illustration of the X-ray tube 3 is omitted for convenience of description. FIG. 6 illustrates on the left thereof the visible light beams whose spread is restricted. The visible light beams pass through the fully-opened collimator 3a. In this manner, the spread of the visible light beams is restricted although the collimator 3a is fully opened. This case does not depend on types of the X-ray tube 3 provided in the X-ray apparatus. Consequently, when the X-ray tube 3 emitting narrow X-ray beams is adopted, the visible light beams passing through the fully-opened collimator 3a is made wider than the X-ray beams. Such a phenomenon may occur. FIG. 6 illustrates this state on the right thereof. Specifically, FIG. 6 illustrates on the right thereof an irradiation condition of the visible light beams by solid lines, and an irradiation condition of X-ray beams by dotted lines.

Figure 7:
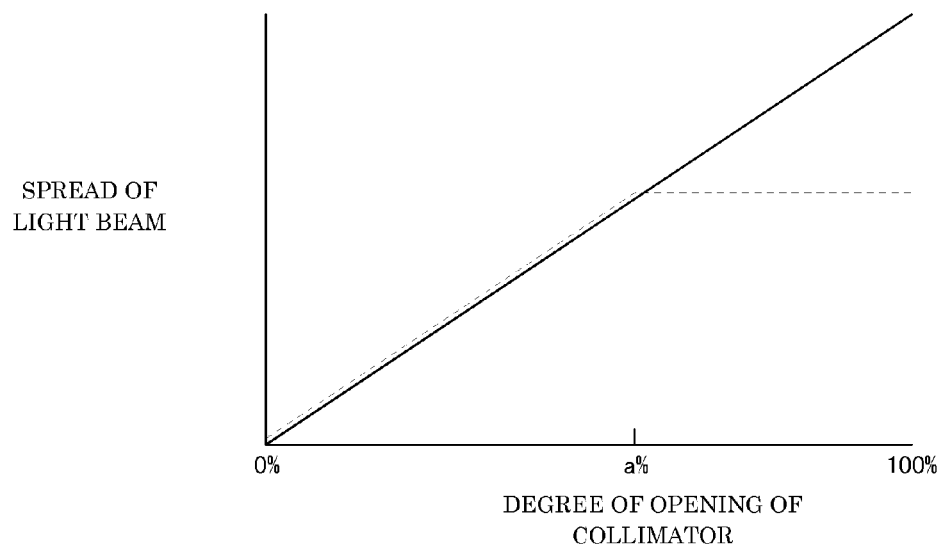

Such a phenomenon does not necessarily occur when the collimator 3a is fully opened. FIG. 7 illustrates a relationship between the degree of opening of the collimator 3a and the spread of the visible light beams and X-ray beams. In a graph, the spread of the visible light beams is represented by solid lines. When the degree of opening is zero, no visible light beam spreads. The degree of opening gradually increases from this condition. Accordingly, the spread of the visible light beams increases monotonously. When the degree of opening reaches 100%, the visible light beams has the maximum spread.

FIG. 7 illustrates the spread of X-ray beams by dotted lines. When the degree of opening is zero, no X-ray beams spread. The degree of opening increases gradually from this condition. Accordingly, similar to the visible light beams, the spread of X-ray beams increases monotonously. On the other hand, when the degree of opening of the collimator 3a increases to a certain level, the spread of X-ray beams does not increases any more and becomes constant although the degree of opening of the collimator 3a increases. That is, the spread of X-ray beams does not change because it is impossible to increase the width of X-ray beams any more outputted from the X-ray tube 3. The degree of opening of the collimator 3a gradually increases to reach the minimum degree of opening at which the spread of X-ray beams does not increase any more. The minimum degree of opening is referred to as a degree of saturation.

When the visible light beams do not conform to the X-ray beams, the following problem may arise. Specifically, when the visible light beams are emitted upon radiography by the operator, the spread of the visible light beams at this time does not represent the spread of X-ray beams. In other words, the operator cannot perform desired radiography. Such a phenomenon should be avoided in view of prevention of needless X-ray exposure.

<Suppression of Unconformity in Spread of Beams>

Consequently, in Embodiment 1, the collimator controller 8 is devised. Specifically, the collimator controller 8 controls the collimator activating mechanism 7 such that the degree of opening of the collimator 3a is lower than the spread of the X-ray beams emitted from the X-ray tube 3.

Specifically, the collimator controller 8 reads out information on the degree of opening stored in the storing unit 28, the information representing the upper limit of the degree of opening of the collimator, and controls the degree of opening of the collimator 3a so as not to exceed the upper limit of the degree of opening. The upper limit of the degree of opening is obtainable through geometric calculation from the spread of X-ray beams emitted from the X-ray tube 3 provided in the apparatus and a distance between a focus of the X-ray tube 3 and the shielding vanes 3b of the collimator 3a. The upper limit of the degree of opening conforms to the degree of opening of saturation. Specifically, the upper limit of the degree of opening is the minimum degree of opening at which the spread of X-ray beams is constant in FIG. 7. The upper limit of the degree of opening is denoted by a %. That is, the minimum degree corresponds to the upper limit of the degree of opening. The degree of opening of the collimator 3a gradually increases while the X-ray tube 3 emits X-ray beams to reach the minimum degree of opening at which the spread of X-ray beams does not increase any more. The storing unit 28 stores the upper limit of the degree of opening.

With Embodiment 1, the collimator controller 8 changes the degree of opening of the collimator 3a from zero to a % as the upper limit of the degree of opening. Consequently, in Embodiment 1, no phenomenon occurs that the visible light beams emitted from the collimator 3a are wider than the X-ray beams.

<Actual Collimator Controller>

The following describes actual operation of the collimator controller 8. The collimator controller 8 receives the detection area set by the area setting unit 11. The detection area represents a length of a film of the cassette 4 in the body axis direction A. Then the collimator controller 8 determines through geometric calculation a required level of the degree of opening of the collimator 3a in the body axis direction A for reaching the X-rays on the entire detection area. At this time, the collimator controller 8 adopts a distance from the X-ray tube 3 to the cassette 4. The distance is stored in the storing unit 28. In this manner, the collimator controller 8 determines the level of the degree of opening of the collimator 3a necessary for radiography using the cassette 4 designated by the operator. The determined degree of opening is referred to as a required degree of opening. For the required degree of opening, the minimum degree of opening necessary for emitting the entire detection area of the cassette 4 is adopted. This prevents the X-ray beams from passing beyond the end of the cassette 4, leading to avoid needless exposure to the subject M. Here, the required degree of opening corresponds to the degree of opening of the collimator 3a necessary for radiography to be conducted by the operator.

The collimator controller 8 compares the required degree of opening with the upper limit of the degree of opening. When the required degree of opening is lower than or equal to the upper limit of the degree of opening, the collimator controller 8 controls the collimator activating mechanism 7 so as to open the collimator 3a to the required degree of opening. When the required degree of opening is higher than the upper limit of the degree of opening, the collimator controller 8 controls the collimator activating mechanism 7 so as to open the collimator 3a to the upper limit of the degree of opening. Then the collimator controller 8 informs the alarm-activation controller 14 so as to activate an alarm. The alarm-activation controller 14 corresponds to the alarm-activation controller in the present invention.

<Regarding Alarm Function>

The following describes an alarm function according to Embodiment 1. An alarm 13 is provided for notifying the operator by producing noises. This causes the operator to notice that radiography is to be conducted requiring X-rays having the maximum width or more that the X-ray tube 3 can output. Control of the alarm 13 is to be described. When the degree of opening of the collimator 3a is controlled so as to exceed the upper limit of the degree of opening, the alarm-activation controller 14 controls the alarm 13 to activate an alarm. The alarm-activation controller 14 controls the alarm activation in accordance with information from the collimator controller 8. Specifically, the collimator controller 8 sends to the alarm-activation controller 14 information that the required degree of opening exceeds the upper limit of the degree of opening. The alarm-activation controller 14 controls the alarm 13 to activate an alarm in accordance with the information. The alarm 13 corresponds to the alarm-activating device in the present invention.

A console 26 (see FIG. 1) is provided for inputting operator's instructions such as start of emitting X-rays. Moreover, a main controller 27 (see FIG. 1) is provided for performing an overall control of each controller. The main controller 27 has a CPU, and implements the X-ray tube controller 6 and each unit by executing various programs. The above units may each be divided into arithmetic units that perform their functions. The storing unit 28 (see FIG. 1) stores all parameters with respect to control of the apparatus such as information on the upper limit of the degree of opening.

<Operation of X-Ray Apparatus>

The following describes operation of the X-ray apparatus 1. As illustrated in FIG. 8, for performing radiography to the subject M with the X-ray apparatus 1, the subject M is firstly placed in the apparatus (placing step S1), and then a radiography mode is selected via the console 26 (selecting step S2). Thereafter, a degree of opening of the collimator 3a is automatically controlled in accordance with the selected radiography mode (collimator controlling step S3). Then a light source in the X-ray tube 3 is turned on for applying visible light (visible light applying step S4). Finally, the X-ray tube 3 emits X-rays to perform radiography (X-ray emitting step S5). Each of these steps will be described in order.

<Placing Step S1, Selecting Step S2>

Firstly, the subject M is placed in the X-ray apparatus 1 (see FIG. 1). Then, the operator inputs a type of the cassette 4 to be used for radiography via the console 26.

<Collimator Controlling Step S3>

When the operator finished inputting via the console 26, the collimator controller 8 controls the degree of opening of the collimator 3a. Specifically, when the required degree of opening necessary for radiography using the designated cassette 4 is less than or equal to the upper limit of the degree of opening, the collimator controller 8 controls the degree of opening of the collimator 3a to be the required degree of opening. When the required degree of opening exceeds the upper limit of the degree of opening, the collimator controller 8 controls the degree of opening of the collimator 3a to be the upper limit of the degree of opening, and controls the alarm-activation controller 14 to activate an alarm. Operation of the collimator controller 8 at this time has already been described.

<Visible-Light Applying Step S4>

When the degree of opening of the collimator 3a is controlled, the X-ray tube controller 6 turns on the visible light source 9 attached to the X-ray tube 3. The visible light beams emitted from the visible light source are reflected on the mirror 15 included in the collimator 3a. The visible light beams spread from the position as a mirror image of the X-ray tube 3 in a focus position by the mirror 15 as the center toward the collimator 3a. Then, the collimator 3a restricts the spread of the visible light, and the visible light is applied to a part of the subject M. The operator can confirm the invisible irradiation area of X-rays prior to X-ray application by visibly confirming the irradiation area of the visible light.

<X-rays Irradiation Step S5>

When the operator issues a command to start irradiation with X-rays via the console 26, the X-ray tube controller 6 controls the visible light source in the X-ray tube 3 to be turned off. Simultaneously, the operator issues another command to irradiate the X-ray tube 3 with X-rays. At this time, the X-ray tube controller 6 controls the X-ray tube 3 under a condition of controlling the X-ray tube depending on a selected site of the subject. The X-rays from the X-ray tube 3 are collimated with the collimator 3a, and then pass through the subject M into the cassette 4. In this manner, radiography is completed.

As noted above, the embodiment of the present invention includes the X-ray tube 3, the collimator 3a, and the visible light source 9. The collimator 3a is provided for restricting the spread of X-rays. The visible light source 9 is provided for representing the area where X-rays are applied instead of the X-ray tube 3 by applying visible light passing through the collimator 3a, the X-rays from the X-ray tube 3 being invisible. With some type of the X-ray tube 3, the spread of the visible light beams through the collimator 3a opening too largely may not possibly conform to the spread of X-rays. Such a situation may occur when the apparatus is provided with the X-ray tube 3 that emits narrow X-rays.

In order to avoid such a situation, the embodiment of the present invention sets the upper limit of the degree of opening as the upper limit of the degree of opening of the collimator 3a. The degree of opening of the collimator 3a gradually increases while the X-rays are emitted to reach the minimum degree of opening at which the spread of X-rays does not increased any more. The minimum degree corresponds to the upper limit of the degree of opening. In the embodiment of the present invention, the irradiation area of the visible light beams always conforms to the irradiation area by the X-ray tube 3. Accordingly, there is no need to perform further radiography. This achieves the X-ray apparatus that allows suppression in needless exposure of X-rays to the subject M.

As noted above, the alarm is activated when the degree of opening of the collimator 3a is controlled so as to exceed the upper limit of the degree of opening. This obtains the apparatus with a higher degree of safety, ensuring to suppress needless exposure.

Moreover, the alarm is activated when the degree of opening of the collimator required upon radiography by the operator exceeds the upper limit of the degree of opening. This obtains accurate notification of the operator.

The present invention is not limited to the above, but may be modified as under.

(1) In the above embodiment, the type of the cassette 4 is identified, and the degree of opening of the collimator 3a is controlled in accordance with the type. However, the present invention is not limited to this. Specifically, the operator may control the degree of opening of the collimator 3a via the console 26. At this time, the degree of opening of the collimator 3a designated by the operator is adopted as a designated degree of opening. In this modification, the collimator controller 8 operates using the designated degree of opening instead of the required degree of opening. That is, the collimator controller 8 compares the designated degree of opening with the upper limit of the degree of opening. When the designated degree of opening is lower than or equal to the upper limit of the degree of opening, the collimator controller 8 controls the collimator activating mechanism 7 to open the collimator 3a to the designated degree of opening. When the designated degree of opening is higher than the degree of opening, the collimator controller 8 controls the collimator activating mechanism 7 to open the collimator 3a to the upper limit of the degree of opening. Then, the collimator controller 8 controls the alarm-activation controller 14 to activate an alarm. Such a construction achieves more flexible control to provide the X-ray apparatus that allows radiography easily.

(2) In the embodiment, the storing unit 28 stores one type of upper limit of the degree of opening. However, the present invention is not limited to this. Specifically, the storing unit 28 may store a plurality of upper limit of the degrees of opening in association with types of X-ray tube 3. In the construction, the X-ray tube controller 6 holds type information representing the types of X-ray tube 3. The X-ray tube controller 6 outputs the type information to the collimator controller 8. The collimator controller 8 reads the upper limit of the degree of opening, corresponding to the obtained type information, from the storing unit 28. Here, the collimator controller 8 performs no control to the collimator 3a prior to reading the upper limit of the degree of opening from the storing unit 28. That is, it is sufficient to obtain the type information as above once when the X-ray apparatus 1 is set in an examination room. After the type information is given and received once, the collimator controller 8 can read out the upper limit of the degree of opening, corresponding to the type of X-ray tube 3, from the storing unit 28. As in this modification, the collimator controller 8 reads out the upper limit of the degree of opening corresponding to the types of X-ray tube 3. This achieves the apparatus with more flexibility. That is, the collimator is surely controlled regardless of types of the X-ray tube 3 provided in the apparatus in accordance with the upper limit of the degree corresponding to the type.

(3) The embodiment mentioned above describes control of the degree of opening of the collimator 3a in the body axis direction A of the cassette 4. Alternatively, the collimator 3a may be controlled similarly in the body side direction S. In this construction, the collimator controller 8 reads out the upper limit of the degree of opening in the body side direction S from the storing unit 28. Then the area setting unit 11 determines a detection area in the body side direction S through input by the operator. Thereafter, the collimator controller 8 compares a required degree of opening determined from the detection area with the upper limit of the degree of opening, and operates similarly to the above.

(4) The foregoing embodiments discuss an apparatus for medical use. The present invention is applicable also to an apparatus for industrial use or for the nuclear field.

(5) X-rays described in the foregoing embodiments are an example of radiation in the present invention. Therefore, the present invention may be adapted also to radiation other than X-rays.

INDUSTRIAL APPLICABILITY

As noted above, the radiographic apparatus of the present invention is suitable for the medical field.

REFERENCE SIGN LIST

3 X-ray tube (radiation source)
3a collimator
4 cassette (detecting device)
6 X-ray tube controller (radiation source controller)
7 collimator activating mechanism (collimator activating device)
8 collimator controller (collimator controller)
9 visible light source
10 visible light source controller (visible light source controller)
11 area setting unit (area setting device)
13 alarm (alarm-activating device)
14 alarm-activation controller (alarm-activation controller)
26 console (input device)
28 storing unit (storing device)

The invention claimed is:

1. A radiographic apparatus, comprising:
an x-ray source configured to emit x-ray;
a detecting device configured to detect the x-ray passing through a subject;
a collimator configured to restrict the spread of the x-ray emitted from the x-ray source;
a collimator activating device configured to activate the collimator to change a degree of opening of the collimator;
a visible light source provided on the collimator and configured to emit visible light beams which pass through a space between shielding vanes of the collimator;
a visible light source controller configured to control the visible light source;
a calculation device configured to calculate an upper limit of the degree of opening based on spread of the x-ray emitted from the x-ray source; and a collimator controller configured to control the collimator activating device so that the spread of the x-ray does not exceed the upper limit of the degree of opening.

2. The radiographic apparatus according to claim 1, further comprising:
an input device via which an operator inputs a command;
an alarm-activating device configured to activate an alarm to the operator; and
an alarm-activation controller configured to issue a command to the alarm-activating device to activate the alarm, the alarm-activation controller controlling the alarm-activating device to activate the alarm when the degree of opening of the collimator is controlled to exceed the upper limit of the degree of opening via the input device.

3. The radiographic apparatus according to claim 2, wherein the collimator controller informs the alarm-activation controller so as to activate the alarm when a required degree of opening exceeds the upper limit of the degree of opening, the required degree of opening being a degree of opening of the collimator required upon radiography to be conducted by the operator.

4. The radiographic apparatus according to claim 1, further comprising:
a storing device configured to store a plurality of upper limits of degrees of opening in association with types of the x-ray source; and
an x-ray source controller configured to control the x-ray source, wherein
the x-ray source controller outputs type information representing one of the types of the x-ray source to the collimator controller, and
the collimator controller reads out one of the plurality of upper limits of the degrees of opening, corresponding to the obtained type information, from the storing device.

5. A radiographic apparatus, comprising:
an x-ray source configured to emit x-ray;
a detecting device configured to detect the x-ray passing through a subject;
a visible light source provided on the collimator and configured to emit visible light beams,
a visible light source controller configured to control the visible light source; and
a collimator configured to restrict the spread of the x-ray from the x-ray source and the spread of the visible light beams from the visible light source;
a collimator activating device configured to activate the collimator to change a degree of opening of the collimator;
a calculation device configured to calculate an upper limit of the degree of opening based on spread of the x-ray emitted from the x-ray source; and
a collimator controller configured to control the collimator activating device to change the degree of opening of the collimator within the upper limit in order for an area illuminated by the visible light beams not to exceed a maximum irradiation area of the x-ray source.

6. The radiographic apparatus according to claim 5, further comprising:
an input device through which an operator inputs a command;
an alarm-activating device configured to activate an alarm to the operator; and
an alarm-activation controller configured to issue a command to the alarm-activating device to activate the alarm when the degree of opening of the collimator is controlled to exceed the upper limit of the degree of opening via the input device.

7. The radiographic apparatus according to claim 6, wherein the collimator controller controls the alarm-activation controller to activate the alarm when a required degree of opening exceeds the upper limit of the degree of opening, the required degree of opening being a degree of opening of the collimator required upon radiography to be conducted by the operator.

8. The radiographic apparatus according to claim 5, further comprising:
a storing device configured to store a plurality of upper limits of degrees of opening in association with types of the x-ray source; and
an x-ray source controller configured to control the x-ray source, wherein
the x-ray source controller outputs type information representing one of the types of the x-ray source to the collimator controller, and
the collimator controller reads out one of the plurality of upper limits of the degrees of opening, corresponding to the obtained type information, from the storing device.

* * * * *